(12) United States Patent
Sanchez

(10) Patent No.: US 10,345,288 B2
(45) Date of Patent: Jul. 9, 2019

(54) MAGNETOPHORESIS SYSTEM FOR SEPARATION OF BIOLOGICAL PARTICLES

(71) Applicant: Pablo Albertos Sanchez, Riverside, CA (US)

(72) Inventor: Pablo Albertos Sanchez, Riverside, CA (US)

( * ) Notice: Subject to any disclaimer, the term of this patent is extended or adjusted under 35 U.S.C. 154(b) by 44 days.

(21) Appl. No.: 15/135,415

(22) Filed: Apr. 21, 2016

(65) Prior Publication Data

US 2017/0030887 A1 Feb. 2, 2017

(51) Int. Cl.

| | | |
|---|---|---|
| *G01N 33/483* | (2006.01) | |
| *G01N 15/14* | (2006.01) | |
| *G01N 33/543* | (2006.01) | |
| *G01N 35/00* | (2006.01) | |
| *G02B 21/02* | (2006.01) | |
| *G02B 21/08* | (2006.01) | |
| *G02B 21/16* | (2006.01) | |
| *G02B 21/34* | (2006.01) | |
| *G02B 21/36* | (2006.01) | |

(52) U.S. Cl.
CPC ..... *G01N 33/4833* (2013.01); *G01N 15/1468* (2013.01); *G01N 33/54326* (2013.01); *G01N 35/0098* (2013.01); *G02B 21/02* (2013.01); *G02B 21/082* (2013.01); *G02B 21/16* (2013.01); *G02B 21/34* (2013.01); *G02B 21/361* (2013.01); *G02B 21/365* (2013.01)

(58) Field of Classification Search
CPC ........ B01L 3/502761; G01N 33/54326; G01N 35/0098
See application file for complete search history.

(56) References Cited

U.S. PATENT DOCUMENTS

| | | | |
|---|---|---|---|
| 5,876,593 A | 3/1999 | Liberti | |
| 6,013,532 A | 1/2000 | Liberti | |
| 7,484,880 B2* | 2/2009 | Cleveland | ........... B01F 13/0818 366/273 |
| 2007/0166835 A1* | 7/2007 | Bobrow | ............... C12Q 1/6834 436/174 |
| 2011/0212440 A1 | 9/2011 | Vivoy | |

FOREIGN PATENT DOCUMENTS

CN 103492081 1/2014

OTHER PUBLICATIONS

Schreier, Stefan et al. "Development of a magnetic bead fluoresence microscopy immunoassay to detect and quantify Leptospira in environmental water samples." Acta Tropica (2012) 122119-125. (Year: 2012).*
Schultz, Nadja et al. "Spectrophotometric assay for online measurement of the activity of lipase immobilised on micro-magnetic particles." Biotechnol. Letters (2007) 29 365-371. (Year: 2007).*

* cited by examiner

*Primary Examiner* — Christopher Adam Hixson
(74) *Attorney, Agent, or Firm* — UCLA Patent Law Clinic

(57) ABSTRACT

A magnetophoresis system for separation of biological particles for the purpose of analysis. A magnetic field is used to separate magnetically functionalized particles from a larger sample. Once separated, an analytic instrument analyzes the separated particles. Embodiments of the system analyze cells of interest using a microscope.

13 Claims, 6 Drawing Sheets

MAGNETOPHORESIS SYSTEM FOR SEPARATION OF BIOLOGICAL PARTICLES

BACKGROUND

Field of the Technology

The invention relates to the field of cell sorting and analysis of microscopic biological entities. More particularly, the invention relates to the magnetic separation of microscopic biological entities and then the subsequent analysis of such separated entities, namely, CPC B03C 1/0332, 1/288, 1/035, 1/0335, 2201/18; C12N 13/00; G01N 15/1459, 2015/149, 2015/1006.

Brief Description of the Field

Antibodies are proteins that bind to specific antigens. An antigen is a specific molecule that could be present on a cell membrane, an organelle, a particular protein, etc. The antibody-antigen interaction is similar to that of a lock and key, in that there is usually only one, or very few, antigens that will bind to a specific antibody. This makes antibodies an excellent tool for identifying and labeling biological species of study.

For example, in a particular population of cells, some portion of cells may express a particular antigen that the others do not. Using a florescent antibody that binds to that particular antigen, one could incubate the population of cells with this antibody, which would bind only to the cells which expressed that particular antigen. After washing away the excess antibody, those cells expressing the antigen and thus being bound to florescent antibodies would fluoresce, while those cells not expressing the antigen would not fluoresce.

Antibodies are an extremely powerful tool for biological research, medical diagnosis, disease therapy, etc. There are hundreds of companies who manufacture and sell antibodies and there are hundreds of thousands of different antibodies that are commercially available. For example, Abnova Corporation manufactures and sells more than 50,000 antibodies.

Antibodies can be made to be magnetic. Antibodies can be coated with magnetic nanoparticles or can have such particles incorporated into them. These antibodies are then susceptible to magnetic forces. Consequently, whatever the antibody binds to will likewise be susceptible to magnetic forces. For example, after magnetic antibodies bind to a cell expressing their reciprocal antigen, that cell could be pushed or pulled by magnetic forces which are acting upon the antibodies. Because the attached antibodies are susceptible to magnetic forces, the entire cell could be pulled towards a magnetic field.

Cell sorting techniques using magnetic antibodies to sort cells are often called "Magnetic-activated cell sorting", or MACS. A typical MACS procedure would involve first incubating a sample with magnetic antibodies. Cells expressing this antigen then attach to the magnetic antibodies. Afterwards the cell solution is transferred to a column inside of a strong magnetic field. Cells attached to magnetic antibodies (expressing the antigen) are retained in the column, while other cells (not expressing the antigen) flow through and out of the column.

The MACS method described in the preceding paragraph could be used positively or negatively with respect to the particular antigen(s). In positive selection, the cells expressing the antigen(s) of interest are retained in the column and can then be isolated after removing the magnetic field. Positive selection is useful for isolating a particular cell type. In negative selection, the magnetic antibodies are used against surface antigen(s) which are known to be present on cells that are not of interest. After incubating the sample with the magnetic antibodies and running the sample through the column, the cells that are not of interest are retained in the column and can be discarded, while the cells of interest are washed through the column into a separate vessel for further study.

There are many other applications and methods for MACS and they are often combined with other cell sorting techniques such as flow cytometry. There are likewise many manufactures of magnetic antibodies, e.g. Milteny Biotec, Thermo Fisher, etc.

BRIEF SUMMARY

Embodiments of this invention utilize the potential of MACS antibodies for analytic purposes. In one embodiment, a cell sample is incubated with magnetic antibodies binding to an antigen on the cells of interest. These cells are now susceptible to magnetic forces. The sample is then placed in chamber. Extending into the chamber is a magnetizable collection structure. This magnetizable collection structure is a metal plate that becomes magnetized when it is contacted by a magnet located outside of the chamber. Agitation is added to the chamber, causing the sample to move about the chamber. While the sample is moving about the chamber, cells come into contact with the magnetizable collection structure. Those cells with attached magnetic antibodies become bound to the magnetizable collection structure, while those cells not expressing the antigen of interest are not bound to the magnetizable collection structure. A rotating or sliding door then separates the magnetizable collection structure from the chamber. Once separated from the chamber, the magnetizable collection structure is demagnetized by moving the external magnet so that it is no longer in contact with the magnetizable collection structure. This magnet is then moved so as to capture the magnetically susceptible cells within its magnetic field. This magnet pulls the cells upward into a thin glass corridor. This corridor is akin to a microscope slide. Once within the glass corridor, the cells are imaged using an automated camera microscope. In this embodiment the automated microscope moves about the corridor in a grid like fashion, taking pictures of the sample. The pictures are then exported to an external computer for automated analysis.

In some embodiments, an apparatus for analyzing magnetically functionalized particles in a sample may include a chamber containing the magnetically functionalized particles in the sample, an analytic instrument communicating with the chamber to receive the magnetically functionalized particles in the sample for analysis, a magnetizable collection structure within the chamber for collecting magnetically functionalized particles from the sample, and a magnetic field source which removes the magnetically functionalized particles from the magnetizable collection structure and forces them to the analytic instrument where the magnetically functionalized particles are analyzed free of attachment to the magnetizable collection structure.

In some embodiments, the analytic instrument is a microscope.

In some embodiments, the microscope is selected from: a conventional microscope, fluorescent microscope, confocal microscopy, or laser scanning microscopy.

In some embodiments, the analytic instrument is a spectrophotometer.

In some embodiments, the magnetizable collection structure is isolated within the chamber by means of a door which isolates the magnetizable collection structure from the rest of the chamber.

In some embodiments, the chamber is a bioreactor or cell culture chamber.

In some embodiments, the magnetic field source may include a fixed magnet or an electromagnet.

In some embodiments, the apparatus may further include an agitator in the chamber to increase the likelihood of the magnetically functionalized particles coming into contact with the magnetizable collection structure.

In some embodiments, the apparatus may further include a camera to take an image of the magnetically functionalized particles as analyzed via the microscope.

In some embodiments, the apparatus may further include a computer coupled to the camera.

In some embodiments, the camera exports the image to the computer.

In some embodiments, the particles in the sample are cells, organelles, chromosomes, proteins, nucleic acids, lipids, carbohydrates, inorganic compounds, inorganic salts, or minerals.

In some embodiments, the magnetizable collections structure is separated from the chamber by a wall and the magnetically functionalized particles are collected upon this wall.

The illustrated embodiments of the invention can also be characterized as a method for analyzing a sample may include a) providing a group of magnetically functionalized particles in a sample, b) collecting a selected group of the magnetically functionalized particles on a magnetizable collection structure, c) demagnetizing the magnetizable collection structure, d) using a magnetic field to remove at least a portion of the selected group of magnetically functionalized particles from the magnetizable collection structure, e) using the magnetic field to further move the portion of the selected group of magnetically functionalized particles into an analytic instrument, and f) analyzing the portion of the selected group of magnetically functionalized particles with the analytic instrument.

In some embodiments, the method where providing a group of magnetically functionalized particles in a sample may include providing magnetically functionalized cells, organelles, chromosomes, proteins, nucleic acids, lipids, carbohydrates, inorganic compounds, inorganic salts, or minerals.

In some embodiments, the method where analyzing the portion of the selected group of magnetically functionalized particles with the analytic instrument may include analyzing the portion of the selected group of magnetically functionalized particles with a microscope.

In some embodiments, the method may further include returning the group of magnetically functionalized particles to the sample after being analyzed.

In some embodiments, the method furthering may include moving the group of magnetically functionalized particles from the analytic instrument to a separate chamber.

In some embodiments, the method may further include taking an image of the magnetically functionalized particles with a camera as analyzed via the microscope.

In some embodiments, the method may further include analyzing the results of the analytic instrument analysis with a computer.

In some embodiments, the method where collecting a selected group of the magnetically functionalized particles on a magnetizable collection structure may include isolating the magnetizable collection structure within the sample chamber by means of a door.

In some embodiments, the method may further include agitating the magnetically functionalized particles in the sample chamber to increase the likelihood of the magnetically functionalized particles coming into contact with the magnetizable collection structure in the sample chamber.

In some embodiments, the method may further include a wall separating the magnetizable collection structure from the chamber and the magnetically functionalized particles are collected upon this wall. While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
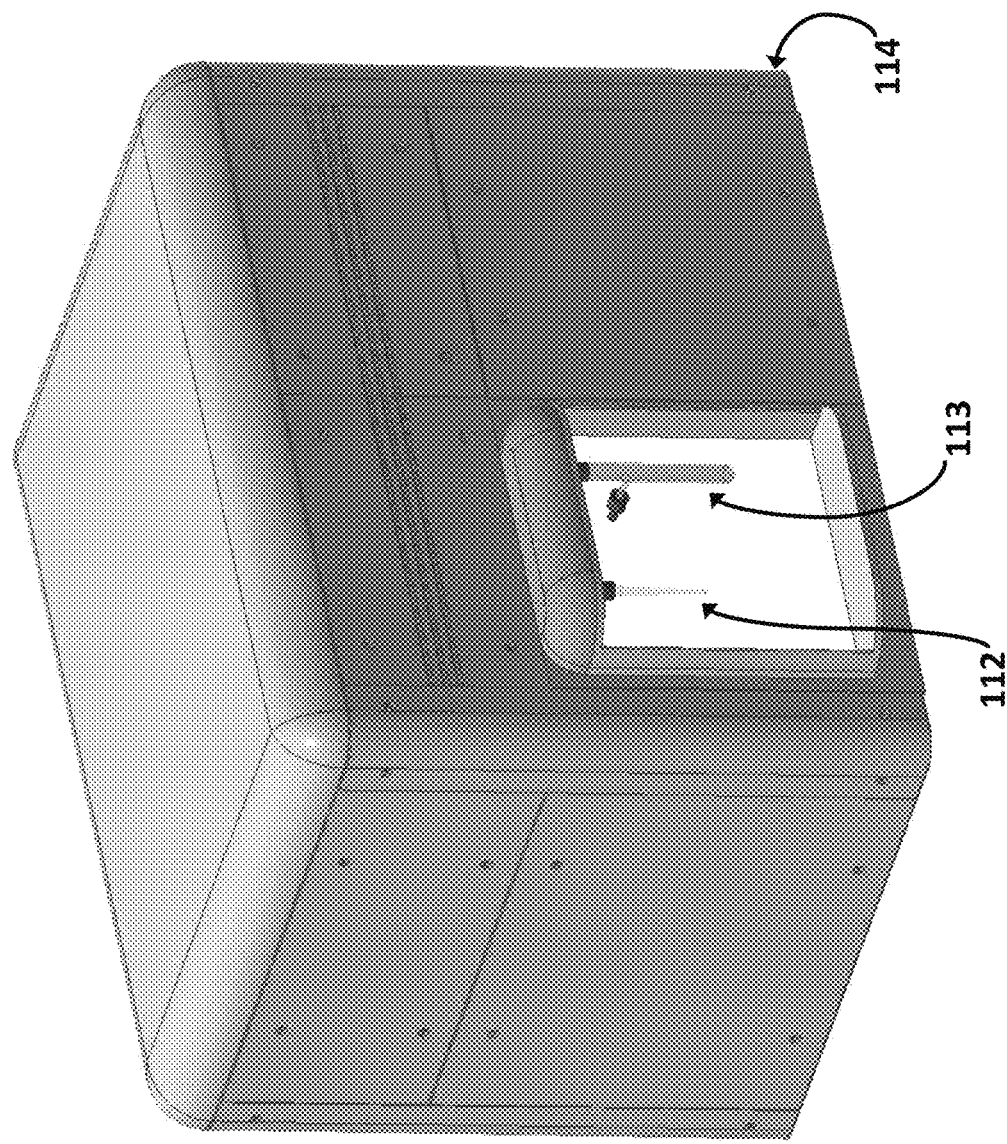
FIG. 1 is an isometric view of a magnetic cell sorting apparatus in accordance with an embodiment of the subject matter. In this view, internal components of the apparatus are hidden from view by an outer covering.
Figure 2:
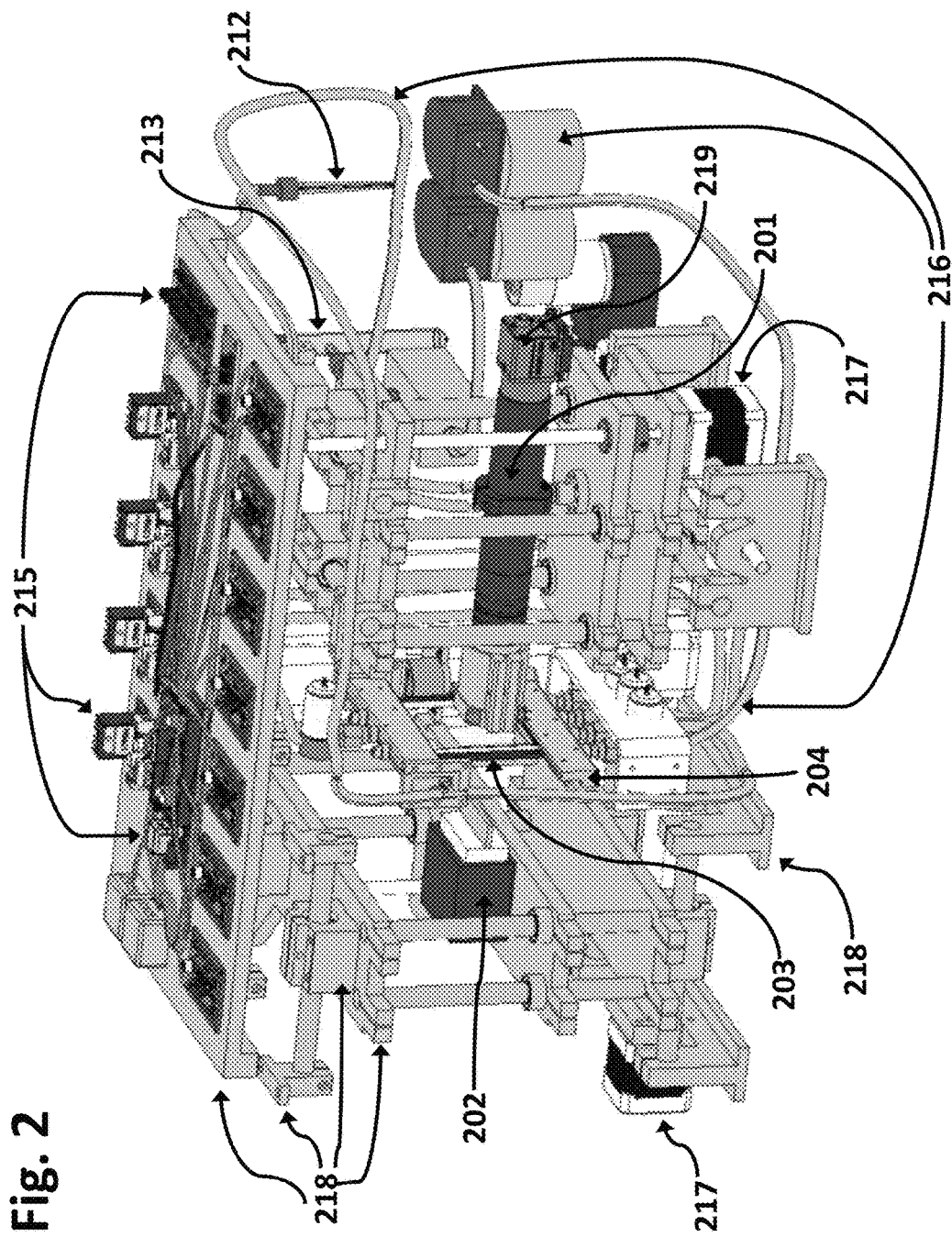
FIG. 2 is an isometric view of a magnetic cell sorting apparatus in accordance with an embodiment of the subject matter. In this view, the outer coverings as seen in FIG. 1 have been removed.

FIG. 1 illustrates an aspect of one embodiment. FIG. 1. Illustrates a manufactured and consumer-ready benchtop embodiment of the subject-matter. Outer covering 114 surrounds and encloses the magnetic cell sorting apparatus as shown in FIG. 2. Outer covering 114 protects the magnetic cell sorting apparatus of FIG. 2. Sample inlet 112 (shown in FIG. 2 as 212) draws a sample into the embodiment for processing. Sample outlet 113 (shown in FIG. 2 as 213) is where a sample is discharged after being analyzed and processed by this embodiment. After being discharged into sample outlet 113, the sample can be removed by an operant.

FIG. 2 illustrates an aspect of one embodiment. FIG. 2 illustrates a magnetic cell sorting apparatus that could be housed inside outer covering 114 of FIG. 1. For the purposes of illustration and simplicity, many functional components of this embodiment have been removed from this figure. Microscope 201 is used to image the sample and is explained in further detail in the proceeding paragraphs. Magnet 202 is used to manipulate portions of the sample and is explained in further detail in the proceeding paragraphs. Narrow glass corridor 203 is used to contain magnetically functionalized particles while they are imaged. Narrow glass corridor 203 is explained in further detail in the proceeding paragraphs. Chamber 204 is used to house and prepare the sample for processing and is explained in further detail in the proceeding paragraphs.

Sample inlet 212 is used to bring a sample into the apparatus for processing. By use of vacuum, this sample is transported through the apparatus by means of various pumps, valves, and associated plumbing. Examples of various pumps, valves, and associated plumbing are shown by label 216. While only several examples of the pumps, valves, and associated plumbing in FIG. 2 are labeled as 216, those of ordinary skill in the art understand that FIG. 2 shows pumps, valves, and associated plumbing that are not labeled 216. These various pumps, valves, and associated plumbing are also used to transport medium and other reactants through the apparatus of this embodiment. After the sample is processed, it is transported by means of plumbing 216 to sample outlet 213. The sample is discharged into sample outlet 213 where it can be collected by an operant.

Control circuitry 215 is used to control the magnetic cell sorting apparatus of this embodiment. Control circuitry 215 controls the various valves and pumps which transport the sample, medium, and other reactants through the apparatus. For example, control circuitry 215 is used to actuate the vacuum pumps used to transport a sample from sample inlet 212 to chamber 204. Furthermore, control circuitry 215 is used to control the stepper motors 217. Stepper motors 217 are used to move magnet 202 and microscope 201. While only several stepper motors 217 have been shown in FIG. 2, those of ordinary skill in the art understand that additional stepper motors may be used to move the various components of this apparatus. Additionally, control circuitry 215 is used to control camera 219. Camera 219 takes images of the sample as viewed through microscope 201. While only several functions of control circuitry 215 have been listed, those of ordinary skill in the art understand that control circuitry 215 is capable of controlling many more features of this embodiment.

Mounting and support brackets are used to mount the magnetic cell sorting apparatus of this embodiment to outer covering 114. Additionally, mounting and support brackets are used hold the internal components of this embodiment together. Furthermore, mounting and support brackets are used to hold linear bearings and other mechanical components that allow for the movement of magnet 202 and microscope 201. Examples of mounting and support brackets are shown in FIG. 2 by label 218. While only several examples of the mounting and support brackets in FIG. 2 are labeled as 218, those of ordinary skill in the art understand that FIG. 2 shows mounting and support brackets that are not labeled 218.

Figure 3:
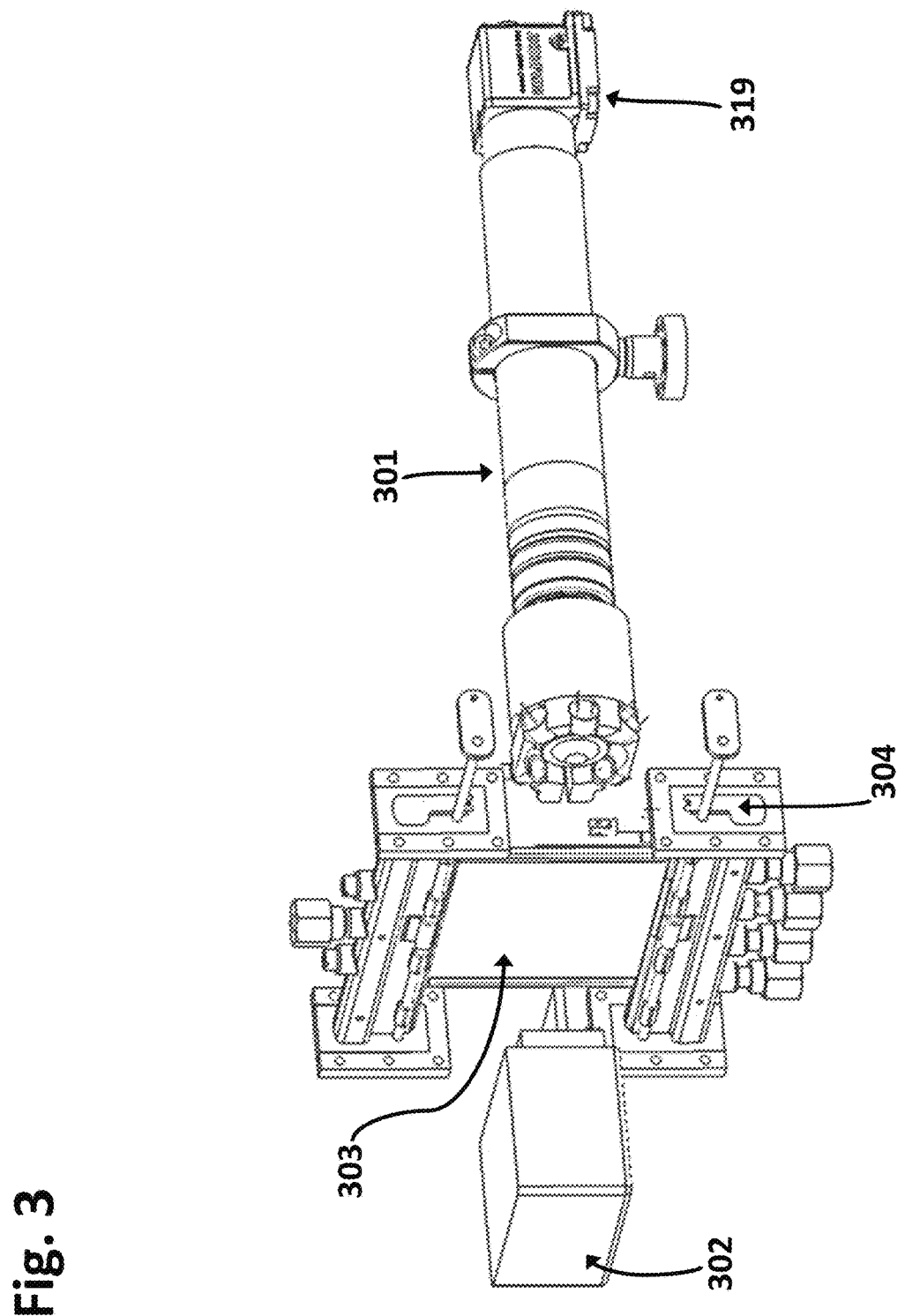
FIG. 3 is isometric view of a magnetic cell sorting apparatus in accordance with an embodiment of the subject matter. In this view, everything except the microscope, magnet, and chamber assemblies have been removed.

FIG. 3 illustrates an aspect of one embodiment. Magnet 302 is used to pull magnetically functionalized particles from chamber 304 into narrow glass corridor 303. Once inside the narrow glass corridor 303, microscope 301 is used to analyze the magnetically functionalized particles. Microscope 301 scans the narrow glass corridor 303 in a grid like pattern taking images of the sample. These images are captured by camera 319 which is attached to microscope 301. In this embodiment, microscope 301 moves to 7348 distinct locations about the narrow glass corridor 303 and thus takes 7348 images of the sample, one image from each location. Those of ordinary skill in the art understand that the analytic instrument of other embodiments may move to a greater or fewer number of locations and take a greater or fewer number of images of the sample.

Figure 4:
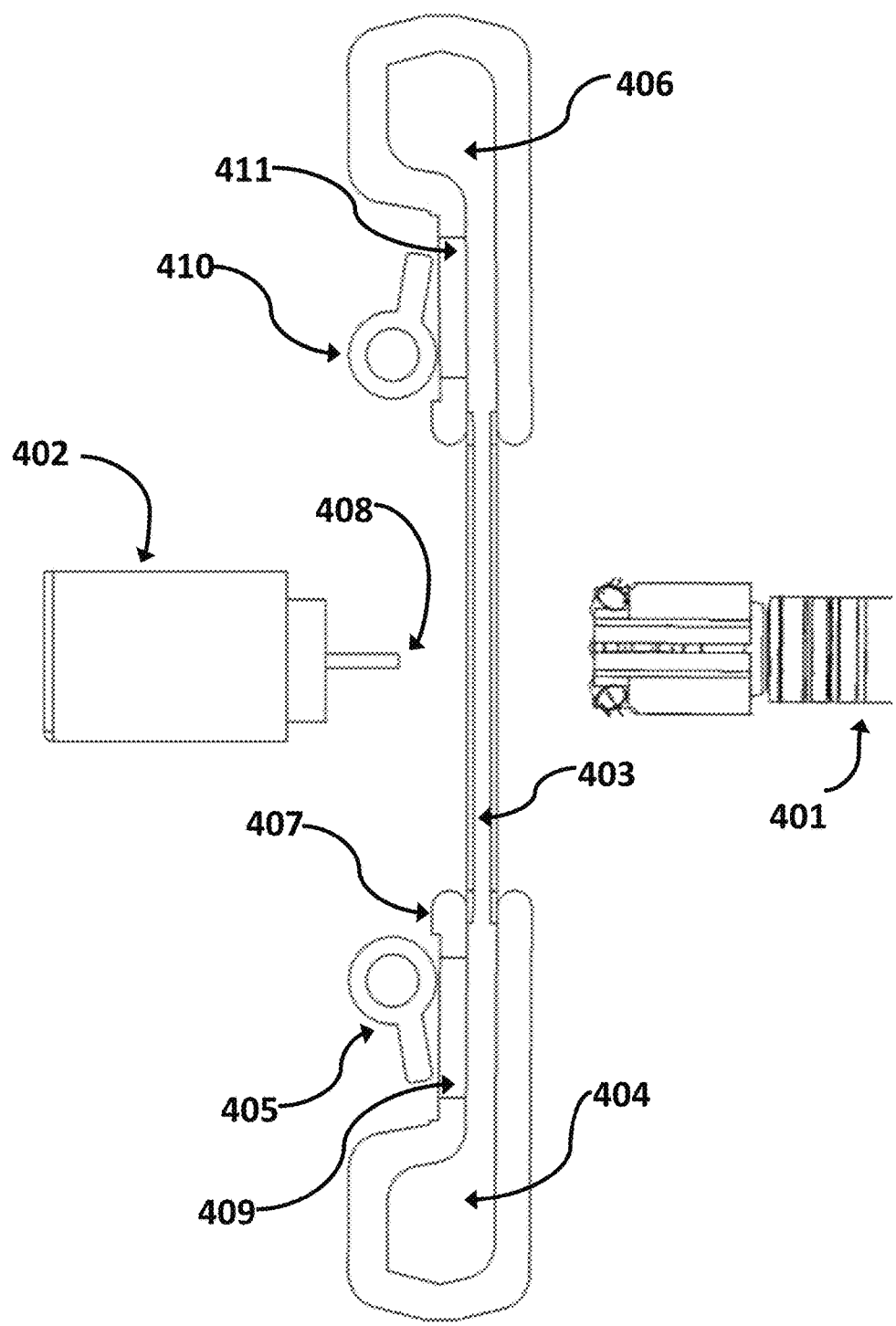
FIG. 4 is a diagrammatic cross sectional view of the chamber in accordance with an embodiment of the subject matter. A magnet and microscope have been added to this view. This diagrammatic view is not drawn to scale.

FIG. 4 illustrates an aspect of one embodiment. By use of vacuum, a sample is sucked from an original vessel to chamber 404. Medium or solvent is then pumped into chamber 404 until this medium or solvent fills up to the top of the narrow glass corridor 403. The pieces of glass forming narrow glass corridor 403 are typically separated by 0.1 millimeters; although this distance can vary based on the relative size of the particles of interest. In embodiments this distance can be changed by the operant for the purpose of analyzing differing sample types.

In one embodiment magnet 402 is capable of moving in two different axes by use of two stepper motors. It is capable of moving closer to or further away from narrow glass corridor 403. It is also capable of moving up and down, along an axis parallel to that of the narrow glass corridor. By moving the magnet 402 into a position so that magnetic protrusion 408 is in contact with magnetizable collection structure 407, magnetizable collection structure 407 becomes magnetized. When magnetizable collection structure 407 is magnetized, magnetically functionalized particles within the chamber 404 will become magnetically bound to magnetizable collection structure 407. In the illustrated embodiment, magnet 402 is a neodymium magnet.

In some embodiments, agitation is added to chamber 404. This agitation causes particles within the sample to move about the chamber 404. This agitation increases the probability of magnetically functionalized particles coming into contact with the magnetizable collection structure 407. In embodiments, this agitation is created by means of a propeller (not shown) within chamber 404. This propeller is powered by means of motor.

In other embodiments, after a desirable amount of magnetically functionalized particles have been collected on magnetizable collection structure 407, door 405 is actuated. Door 405 is actuated by means of a solenoid. Door 405 rotates and pushes on a silicon window 409. Silicon window 409 is flexible. When door 405 pushes on silicon window 409, it is pushed laterally until it is touching the opposite side of chamber 404, creating a seal. When door 405 pushes on silicon window 409, magnetizable collection structure 407 and attached magnetically functionalized particles thus become isolated from the rest of chamber 404.

In some embodiments, magnet 402 is then moved so that magnetic protrusion 408 is no longer touching magnetizable collection structure 407. At this point magnetizable collection structure 407 is no longer magnetized and those magnetically functionalized particles that were previously bound to magnetizable collection structure 407 are free to move off of magnetizable collection structure 407. Because these magnetically susceptible particles are no longer magnetically bound to magnetizable collection structure 407, they can become caught in any local magnetic field; in some embodiments, they are now caught in the magnetic field of magnet 402. This magnetic field is used to push and pull the magnetically functionalized cells into narrow glass corridor 403.

In some embodiments, microscope 401 then analyzes the sample by taking pictures of the magnetically functionalized particles that are within narrow glass corridor 403. Microscope 401 can move in three axis. To move up and down, left and right, and along the narrow glass corridor 403, microscope 401 is moved by two stepper motors. To move closer to and further away from the narrow glass corridor 403, microscope 401 is moved by means of a hand rotated gear. Movement about this axis focuses the microscope. In alternative embodiments, movement about this axis is controlled by a stepper motor. In some embodiments, microscope 401 moves about the narrow glass corridor in a grid pattern, stopping at about 7348 distinct locations, taking an image at each location. These images are taken by camera (not shown) which is attached to microscope 401. These images are then exported to an external computer (not shown).

In one embodiment, after the sample has been imaged, a medium is pumped into second chamber 406. At this point door 410 is now opened by means of a solenoid. When door 410 is opened, it is no longer pushing on silicon window 411, and the medium is present continuously from chamber 404, through narrow glass corridor 403, and into second chamber 406. By moving magnet 402 away from narrow glass corridor 403, and by opening door 410, magnetically functionalized particles within narrow glass corridor 403 tend to move into the medium or solvent in second chamber 406. Furthermore, magnet 402 can be used to push and pull magnetically functionalized particles within narrow glass corridor 403 into second chamber 406. At this point the magnetically functionalized particles in second chamber 406 can be pumped to a separate vessel and removed from the apparatus. In the alternative, by once again creating a vacuum in chamber 404, magnetically functionalized particles and medium in second chamber 406 can be returned to chamber 404. Furthermore, before returning the magnetically functionalized particles in chamber 406 to chamber 404, the residual medium and sample still contained in chamber 404 can be removed from the apparatus by means of a pump to a separate vessel. The magnetically functionalized particles received into chamber 404 from chamber 406 can then be processed again. The sample and medium in the first chamber can then be pumped to a separate vessel and removed from the apparatus.

In some embodiments, chamber 404 is a bioreactor, inside which various cells, cellular components, and byproducts are being produced. In such an embodiment, particles of interest are magnetically functionalized and then removed from the chamber 404 using magnetic collection structure 407 and magnet 402. These cells are pulled from chamber 404, and are then removed from the bioreactor.

In some embodiments, cells are undergoing transdifferentiation in chamber 404. In such an embodiment, transdifferentiated cells are magnetically functionalized and then removed from the chamber 404 using magnetic collection structure 407 and magnet 402. These cells are pulled from chamber 404, and are then removed from the apparatus.

Figure 5A:
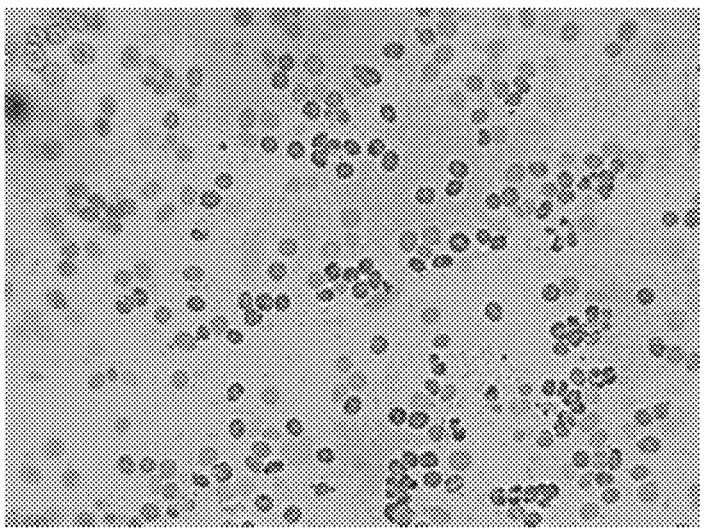
FIGS. 5*a*-5*c* show three examples of pictures of cell samples that were analyzed using an embodiment of the subject matter.
Figure 5B:
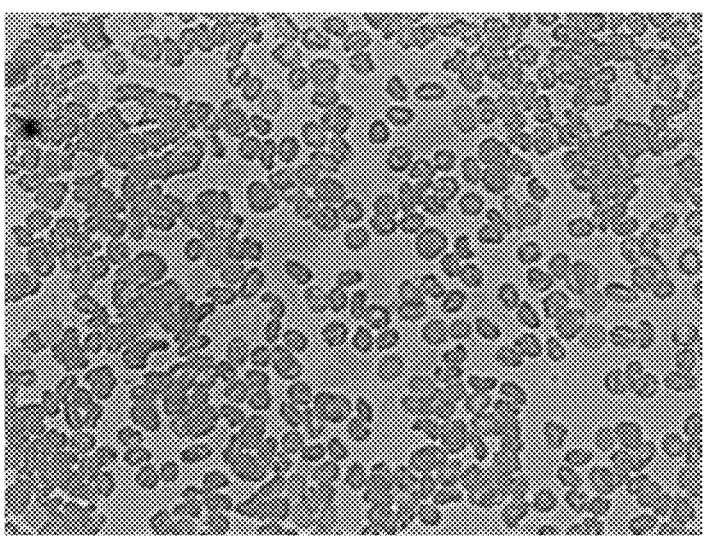
Figure 5C:
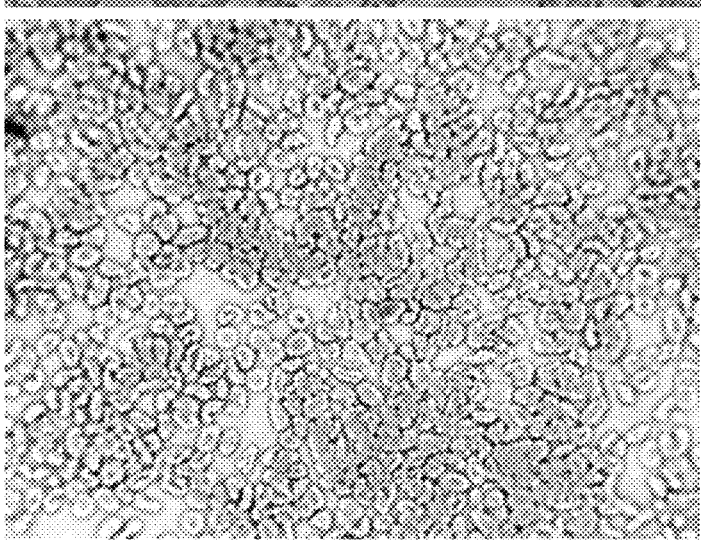

FIGS. 5*a*-5*c* show three pictures taken of samples that were analyzed using an embodiment of the subject matter. Images of FIGS. 5*a*, 5*b*, and 5*c* are of erythrocyte cells as viewed through a microscope in an embodiment at 40× magnification. These images were taken by a camera attached to a microscope of one embodiment.

Figure 6:
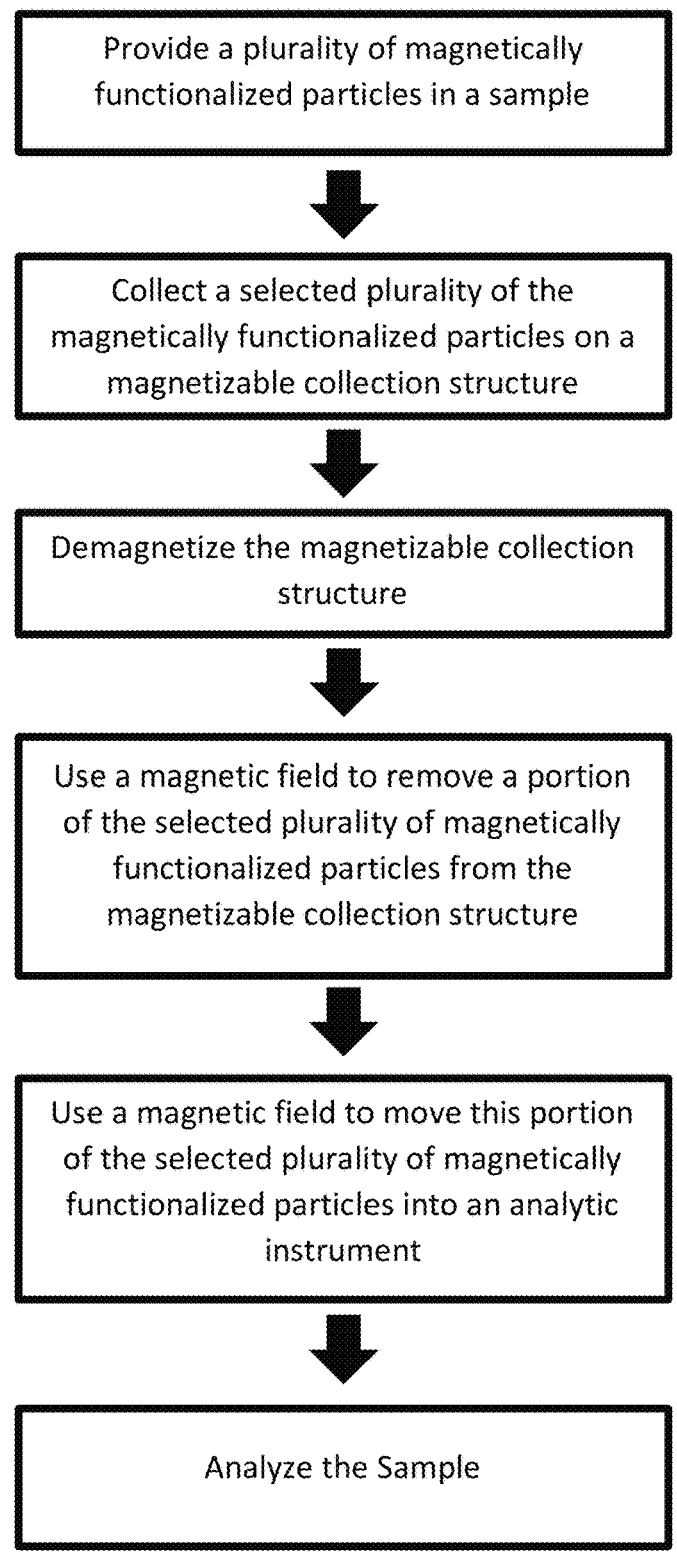
FIG. 6 is a flowchart that explains the steps of an embodiment.

In some embodiments, samples are processed using the steps as exemplified in FIG. 6. Those of ordinary skill in the art understand that other embodiments may process samples in other ways.

The following definitions are provided for the purposes of clarity and illustration. However, the definitions should not be construed to be limiting by excluding applicable dictionary, technical, trade or scientific meanings or usages in the profession or literature.

A "chamber", as used herein, means a feature on or in an article that can contain a fluid. A chamber may be formed from one or multiple parts or pieces. A chamber may have any cross-sectional shape, for example, circular, oval, triangular, irregular, square or rectangular (having any aspect ratio), or the like, and may be covered or uncovered, i.e. open or closed to the external environment surrounding the chamber. A chamber may communicate with any number of other chambers or components. A chamber need not have a definite volume or shape, i.e. it may have the ability to change in size or shape.

"Particle" or "Particles" as used herein, means any particle within a sample. These particles could be a wide variety of different species, such as, as a non-exhaustive list, cells, organelles, viruses, cell aggregates, cell islets, embryos, pollen grains, artificial or natural organic particles such as latex particles, dendrimers, vesicles, nanoparticles, quantum dots, metal microparticles, metal nanoparticles, organometallic micro or nanoparticles, nanotubes, artificial or natural macromolecules, microgels, macromolecular aggregates, proteins or protein aggregates, amino acids, amino acid sequences, natural and artificial proteins, polypeptides, fragments of proteins, protein complexes, enzymes, antibodies, glycopeptides, glycoproteins, polynucleotides or polynucleotide aggregates, nucleoproteic aggregates, polysaccharides, or supramolecular assemblies, histidine tags, hydrophobic moieties, hydrogen-bonding capture moieties, polyelectrolytes, phospholipids, chemicals, drugs, nucleic acids, antibodies, fluorescent moieties, luminescent moieties, dyes, or combinations of the hereabove compounds.

"Magnetically functionalized particle", as used herein, means any particle that is susceptible to magnetic forces. This particle could be inherently susceptible to magnetic forces, e.g. red blood cells, or could be susceptible because it has been bound a magnetic antibody or antibodies, or could be magnetically susceptible through other means. Magnetic antibodies are often created by conjugating magnetic particles to antibodies. These antibodies can bind specifically to particular antigens that are expressed on particles. Once bound, these particles are magnetically functionalized and will be susceptible to magnetic forces. This antibody labeling process could be direct or indirect. In a direct magnetic antibody labeling, magnetic antibodies will bind to the antigens on the particles as described above. An indirect magnetic antibody will be based on a two-step procedure. In the first step, the particles are labeled with a primary antibody that binds to the antigen. In the second step, the magnetic particles are bound to the primary antibody or to a molecule that is conjugated to the primary antibody. After the second step, the particles are magnetically functionalized and will be susceptible to magnetic forces. Magnetic antibody labeling need not be limited to the methods described herein, however. Additionally, magnetically functionalized particles are not limited to particles that have been made magnetically susceptible because of magnetic antibodies. Magnetic antibodies are commercially available for a wide variety of highly specific uses and are manufactured and distributed by many companies, including, but not limited to, Miltenyl Biotec, Thermo Fisher, EMD Millipore, Sigma-Aldrich, etc.

"Magnetizable collection structure", as used herein, means a feature which can become magnetized. A magnetizable collection structure may be formed from one or multiple parts or pieces. A magnetizable collection structure may have any cross-sectional shape, for example, circular, oval, triangular, irregular, square or rectangular (having any aspect ratio). In one embodiment, the magnetizable collection structure is a flat metal plate within and forming part of a chamber. In this embodiment the magnetizable collection structure becomes magnetized when it comes into contact with a magnet.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. An apparatus for analyzing magnetically functionalized particles in a sample comprising:
    a chamber containing the magnetically functionalized particles in the sample;
    an analytic instrument communicating with the chamber to receive the magnetically functionalized particles in the sample for analysis;
    a magnetizable collection structure within the chamber for collecting magnetically functionalized particles from the sample;
    a door configured to isolate the magnetizable collection structure from a rest of the chamber; and
    a magnetic field source which removes the magnetically functionalized particles from the magnetizable collection structure and forces them to the analytic instrument where the magnetically functionalized particles are analyzed free of attachment to the magnetizable collection structure.

2. The apparatus of claim 1 wherein the analytic instrument is a microscope.

3. The apparatus of claim 2 wherein the microscope is selected from: a conventional microscope, fluorescent microscope, confocal microscope, or laser scanning microscopy.

4. The apparatus of claim 1 wherein the analytic instrument is a spectrophotometer.

5. The apparatus of claim 1 wherein the chamber is a bioreactor or cell culture chamber.

6. The apparatus of claim 1 wherein the magnetic field source comprises a fixed magnet or an electromagnet.

7. The apparatus of claim 1 further comprising an agitator in the chamber to increase the likelihood of the magnetically functionalized particles corning into contact with the magnetizable collection structure.

8. The apparatus of claim 2 further comprising a camera to take an image of the magnetically functionalized particles as analyzed via the microscope.

9. The apparatus of claim 1 further comprising a wall, wherein the wall separates the magnetizable collection structure from the chamber and the magnetically functionalized particles are collected upon the wall.

10. The apparatus of claim 1 wherein the particles in the sample are cells, organelles, chromosomes, proteins, nucleic acids, lipids, or carbohydrates.

11. The apparatus of claim 1 wherein the door rotates to isolate the magnetizable collection structure within the chamber from the rest of the chamber.

12. The apparatus of claim 11 further comprising a flexible silicon window, wherein the door pushes on the flexible silicon window to create a seal in isolating the magnetizable collection structure from the rest of the chamber.

13. The apparatus of claim 11 wherein the door rotates using a solenoid.

* * * * *